United States Patent
Zuluaga et al.

(10) Patent No.: US 6,895,137 B2
(45) Date of Patent: May 17, 2005

(54) MULTI-CHANNEL OPTICAL COUPLER FOR SPINNING CATHETER

(75) Inventors: Andres Zuluaga, Boston, MA (US); Brett E. Bouma, Quincy, MA (US)

(73) Assignee: InfraReDx, Inc., Cambridge, MA (US)

( * ) Notice: Subject to any disclaimer, the term of this patent is extended or adjusted under 35 U.S.C. 154(b) by 409 days.

(21) Appl. No.: 10/164,721

(22) Filed: Jun. 7, 2002

(65) Prior Publication Data

US 2003/0228085 A1 Dec. 11, 2003

(51) Int. Cl.[7] .............................. G02B 6/26; A61B 6/00
(52) U.S. Cl. .......................... 385/15; 385/39; 385/26; 385/33; 600/478
(58) Field of Search ............................. 385/15, 25–26, 385/115–117, 14, 118–119, 39, 31–35; 600/478, 101, 160

(56) References Cited

U.S. PATENT DOCUMENTS

| | | | |
|---|---|---|---|
| 4,109,998 A | * 8/1978 | Iverson | 385/26 |
| 4,725,116 A | 2/1988 | Spencer | 350/96.2 |
| 4,872,737 A | 10/1989 | Fukahori et al. | 350/96.2 |
| 4,900,117 A | 2/1990 | Chen | 350/96.15 |
| 4,934,783 A | 6/1990 | Jacobson | 350/96.15 |
| 5,016,961 A | 5/1991 | Aldrich | 350/96.15 |
| 5,073,040 A | 12/1991 | Guinard | 385/36 |
| 5,290,277 A | 3/1994 | Vercimak et al. | 606/15 |
| 5,297,225 A | 3/1994 | Snow et al. | 385/25 |
| 5,319,726 A | 6/1994 | Abney | 385/26 |
| 5,336,897 A | 8/1994 | Watanabe et al. | 250/551 |
| 5,436,988 A | 7/1995 | Narendran | 385/26 |
| 5,535,294 A | 7/1996 | Kamuz et al. | 385/25 |
| 5,568,578 A | * 10/1996 | Ames | 385/34 |
| 5,872,879 A | 2/1999 | Hamm | 385/25 |
| 5,949,929 A | 9/1999 | Hamm | 385/25 |
| 6,113,533 A | 9/2000 | Howes et al. | |
| 6,263,133 B1 | 7/2001 | Hamm | 385/33 |
| 6,301,405 B1 | 10/2001 | Keil | 385/25 |

* cited by examiner

Primary Examiner—Brian Healy
Assistant Examiner—Michael P. Mooney
(74) Attorney, Agent, or Firm—Fish & Richardson P.C.

(57) ABSTRACT

A system for identifying vulnerable plaque includes a catheter having a collection fiber and a delivery fiber extending therethrough. The catheter is engaged to a distal face of a housing configured to spin about an axis. The proximal face of the housing has a central aperture. First and second optical relays extend respectively between the central aperture and a central port on the distal face and between a detector and an eccentric port on the distal face. The central and eccentric ports are in optical communication with the delivery and collection fibers respectively.

22 Claims, 6 Drawing Sheets

MULTI-CHANNEL OPTICAL COUPLER FOR SPINNING CATHETER

FIELD OF INVENTION

This invention relates to catheters, and in particular, to catheters that accommodate more than one optical fiber.

BACKGROUND

Vulnerable plaques are lipid filled cavities that form within the wall of a blood vessel. These plaques, when ruptured, can cause massive clotting in the vessel. The resultant clot can interfere with blood flow to the brain, resulting in a stroke, or with blood flow to the coronary vessels, resulting in a heart attack.

To locate vulnerable plaques, one inserts a catheter through the lumen of the vessel. The catheter includes a delivery fiber for illuminating a spot on the vessel wall and one or more collection fibers for collecting scattered light from corresponding collection spots on the vessel wall. The delivery fiber, and each of the collection fibers form distinct optical channels within the catheter. The catheter used for locating plaques is thus a multi-channel catheter.

In operation, a light source outside the catheter introduces light into the delivery fiber. A detector, also outside the catheter, detects light in the collection fiber and generates an electrical signal representative of that light. This signal is then digitized and provided to a processor for analysis.

A vulnerable plaque can be anywhere within the wall of the artery. As a result, it is desirable to circumferentially scan the illuminated spot and the collection spot around the vessel wall. One way to do this is to spin the multi-channel catheter about its axis. However, since neither the light source nor the processor spin with the catheter, it becomes more difficult to couple light into and out of the delivery and collection fibers while the catheter is spinning.

SUMMARY

The invention features a multi-channel coupler that spins synchronously with a catheter having optical fibers extending through it. Each fiber defines an optical channel. The coupler enables stationary equipment to couple light beams or signals representative of light beams into or out of each fiber separately from all other fibers, even while the catheter spins about its axis.

In one aspect, the invention includes a multi-channel optical coupler having a housing configured to spin about an axis. The housing has a proximal face with a central aperture that intersects the axis. The coupler includes at least two optical relays: a first optical relay that guides the first beam from the central aperture to a central port on the distal face; and a second optical relay for guiding a second beam to a detector from an eccentric port on the distal face.

Some embodiments of the invention include a first optical relay having a stationary lens disposed to direct the first beam onto the central aperture. In some of these embodiments, a focusing lens is disposed between the stationary lens and the central port. In yet other embodiments, the first optical relay includes a graduated index of refraction ("GRIN") lens seated in the central aperture, the GRIN lens being configured to direct the first beam to the central port.

The invention includes embodiments that feature variations of the second optical relay. Among these are embodiments in which the second optical relay includes a collimating lens within the housing. This collimating lens is disposed to guide the second beam entering the housing at the eccentric port toward a detector mounted on an inner wall of the housing. In some of these embodiments, the second optical relay further includes a light-directing element disposed to direct the second beam toward a peripheral wall of the housing.

Additional variations of the second optical relay are those found in embodiments featuring one or more eccentric apertures in the proximal face of the housing. These eccentric apertures allow passage of one or more corresponding second beams. These beams trace paths on an annular mirror outside the housing as the housing spins.

In some embodiments, the annular mirror features a mirror aperture disposed to permit the first beam to pass therethrough. In others, the annular mirror is disposed to direct a path traced by the one or more second beams onto a stationary detector.

Another aspect of the invention is a system for identifying vulnerable plaque. In one embodiment, the system includes a catheter having a collection fiber and a delivery fiber extending therethrough. The catheter engages a distal face of a housing configured to spin about an axis. The proximal face of the housing has a central aperture in optical communication with a central port on the distal face by way of a first optical relay that extends therebetween. A second optical relay extending between a detector and an eccentric port on the distal face provides optical communication with the collection fiber.

In an additional aspect, the invention provides a way to optically couple to a collection fiber and a delivery fiber. In one practice, the method includes transmitting a delivery beam into a central aperture of a housing and guiding the delivery beam from the central aperture to a central port in the housing, the central port being in optical communication with the delivery fiber. A collection beam is then received from an eccentric port in the housing, the eccentric port being in optical communication with the collection fiber. The collection beam is then guided to the detector.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Embodiments of the invention may have one or more of the following advantages. By providing a continuous connection to both optical fibers, the rotary coupler permits the entire circumference of an artery to be scanned automatically.

A rotary coupler having the features of the invention can also be used to identify other structures outside but near a lumen, or on the surface of the lumen wall. For example, cancerous growths within polyps can be identified by a catheter circumferentially scanning the lumen wall of the large intestine, cancerous tissue in the prostate may be identified by a catheter scanning the lumen wall of the urethra in the vicinity of the prostate gland, or Barrett's cells can be identified on the wall of the esophagus. In addition to its medical applications, the rotary coupler can be used in industrial applications to identify otherwise inaccessible structures outside pipes.

Other features and advantages of the invention will be apparent from the following detailed description, and from the claims.

DETAILED DESCRIPTION

System Overview

Figure 1:
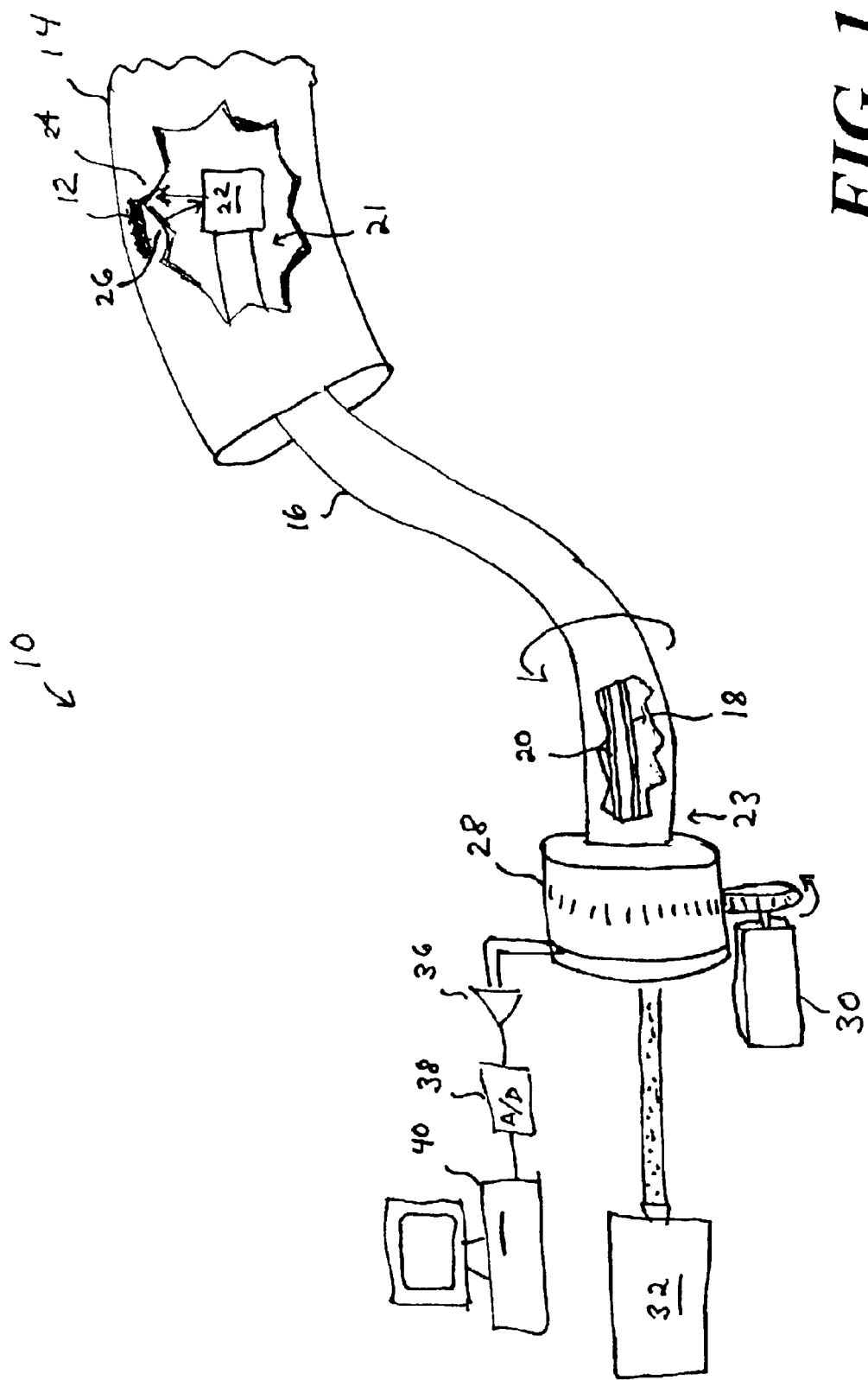
FIG. 1 is a system for identifying vulnerable plaque in a patient.

FIG. 1 shows a diagnostic system 10 for identifying vulnerable plaque 12 in an arterial wall 14 of a patient. The diagnostic system features a catheter 16 to be inserted into a selected artery, e.g. a coronary artery, of the patient. A delivery fiber 18 and a collection fiber 20 extend between a distal end 21 and a proximal end 23 of the catheter 16.

Figure 2:
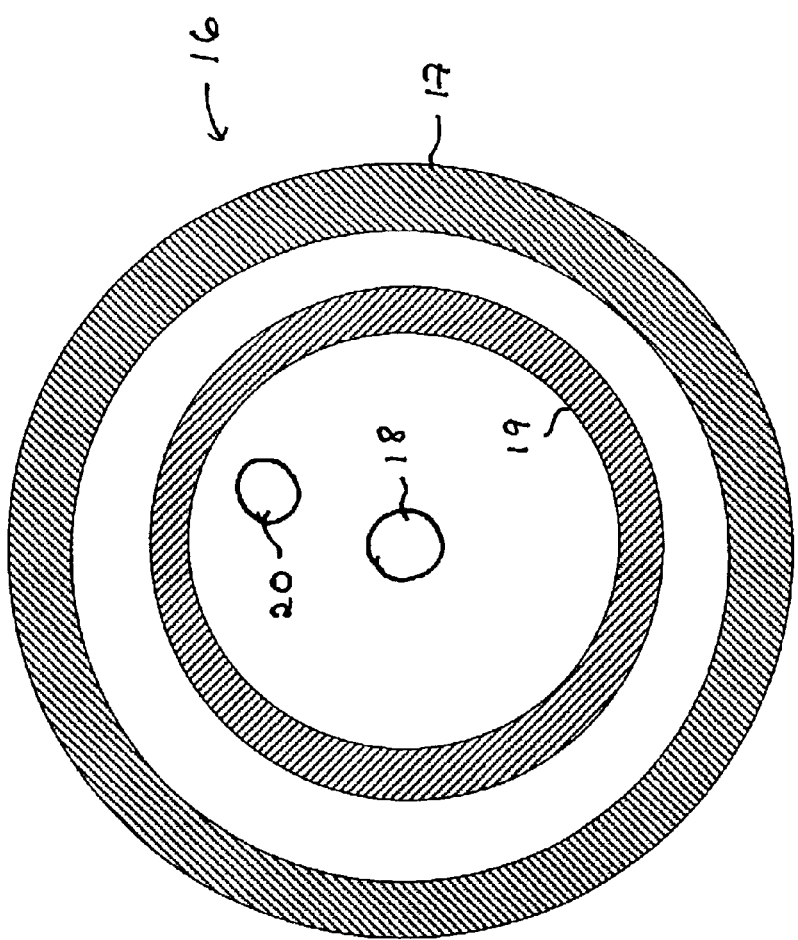
FIG. 2 is a cross-section of the multi-channel catheter in FIG. 1.

As shown in FIG. 2, the catheter 16 includes a jacket 17 surrounding a rotatable core 19. The delivery fiber 18 extends along the center of the core 19 and the collection fiber 20 extends parallel to, but radially displaced from, the delivery fiber 18. The rotatable core 19 spins at rate between approximately 4 revolutions per minute and 30 revolutions per minute.

At the distal end 21 of the catheter 16, a tip assembly 22 directs light traveling axially on the delivery fiber 18 toward an illumination spot 24 on the arterial wall 14. The tip assembly 22 also collects light from a collection spot 26 on the arterial wall 14 and directs that light into the collection fiber 20.

A multi-channel coupler 28 driven by a motor 30 engages the proximal end 23 of the catheter 16. When the motor 30 spins the multi-channel coupler 28, both the coupler 28 and the catheter 16 spin together as a unit. This feature enables the diagnostic system 10 to circumferentially scan the arterial wall 14 with the illumination spot 24.

In addition to spinning the catheter 16, the multi-channel coupler 28 guides light from a laser 32 (or other light source, such as an LED, a super luminescent LED, or an arc lamp) into the delivery fiber 18 and guides light emerging from the collection fiber 20 into one or more detectors (not visible in FIG. 1). The multi-channel coupler 28 performs these tasks even as it spins the catheter 16.

The detectors provide an electrical signal indicative of light intensity to an amplifier 36 connected to an analog-to-digital ("A/D") converter 38. The A/D converter 38 converts this signal into data that can be analyzed by a processor 40 to identify the presence of a vulnerable plaque 12 hidden beneath the arterial wall 14.

Coupler Fixed to Catheter

Figure 3:
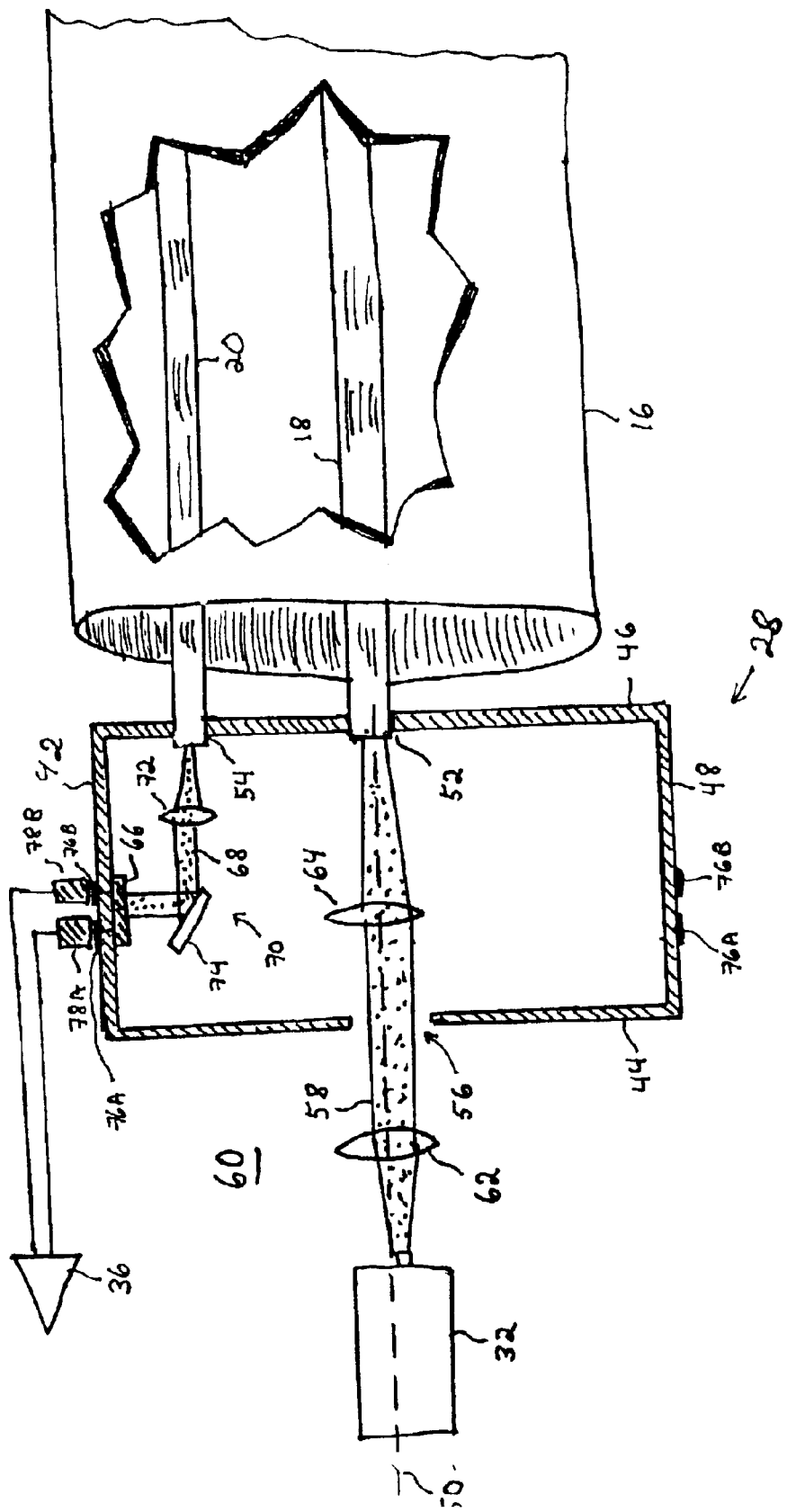
FIGS. 3 and 5–6 are multi-channel couplers incorporating the invention.

A multi-channel coupler 28 for carrying out the foregoing tasks, as shown in FIG. 3, includes a cylindrical housing 42 having a proximal face 44 joined to a distal face 46 by a peripheral wall 48. A bearing (not shown) supports the housing 42 and enables it to spin about an imaginary axis 50 that intersects the proximal and distal faces 44, 46 thereof.

The distal face 46 of the housing 42 is coupled to the catheter 16. Two optical fibers extend through the catheter 16: a delivery fiber 18 for illuminating the arterial wall 14 and a collection fiber 20 that collects light scattered from the arterial wall 14. The catheter 16 and the housing 42 spin together about the same axis 50.

Figure 4:
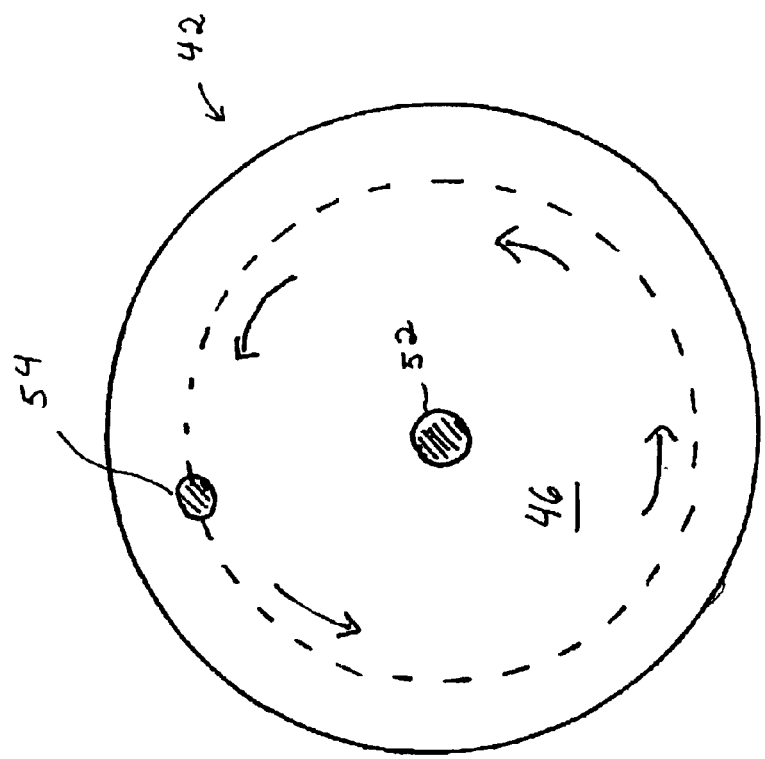
FIG. 4 is an end view of the multi-channel coupler of FIG. 1.

The distal face 46 of the housing 42 has a central port 52 for receiving the delivery fiber 18 and an eccentric port 54 for receiving the collection fiber 20. The central port 52 is located at the intersection of the axis 50 with the distal face 46. The eccentric port 54 is radially displaced from the central port 52. As a result, when the catheter 16 and the housing 42 spin about their common axis 50 the delivery fiber 18 remains stationary and the collection fiber 20 traces out a circular path, as shown in an end view in FIG. 4.

At its intersection with the axis 50, the proximal face 44 has a central aperture 56 for receiving a delivery beam 58 from a laser 32 across a gap 60. The delivery beam 58 can be directed toward the central aperture 56 by pointing a laser 32 as shown, by providing an optical relay to direct the delivery beam 58 to the central aperture 58, or by guiding the delivery beam 58 toward the central aperture 58 along an optical fiber. This central aperture 56, like the central port 52 on the distal face 46, remains stationary even as the housing 42 spins about the axis 50.

A first collimating lens 62 collimates the delivery beam 58 and directs it into the housing 42 through the central aperture 56. A first optical relay 64 within the housing 42 then receives the collimated delivery beam 58 and directs it distally across the housing 42 toward the central port 52, where it enters the delivery fiber 18. As used herein, an optical relay refers to a set of optical elements, such as lenses, prisms, and mirrors, arranged to direct light from a source to a destination.

In FIG. 3, this first optical relay 64 includes a converging lens focused at the central port 28. However, the first optical relay 64 can include components other than, or in addition to that shown in FIG. 1. Between the central port 28 and the central aperture 56, the delivery beam 58 is not constrained to travel along the axis 50 as shown in FIG. 1.

Also within the housing 42, mounted on an interior of the peripheral wall 48, is a detector 66 for receiving a collection beam 68 entering through the eccentric port 54. A second optical relay 70 receives the collection beam 68 from the eccentric port 54 and directs it to the detector 66. In FIG. 3, this second optical relay 70 includes a second collimating lens 72 that receives a diverging collection beam 68 from the eccentric port 34 and directs a collimated collection beam 68 toward a diagonal mirror 74. The diagonal mirror 74 then reflects the collimated collection beam 68 toward the detector 66.

The detector 66 is electrically connected to a pair of slip rings 76A–B on the outer surface of the peripheral wall 48. A corresponding pair of stationary brushes 78A–B provides electrical coupling between the slip rings 76A–B and the amplifier 36. As the housing 42 spins, the brushes 78A–B maintain sliding contact with the slip rings, thereby providing a continuous signal to the amplifier 36.

Detachable Coupler

Figure 5:
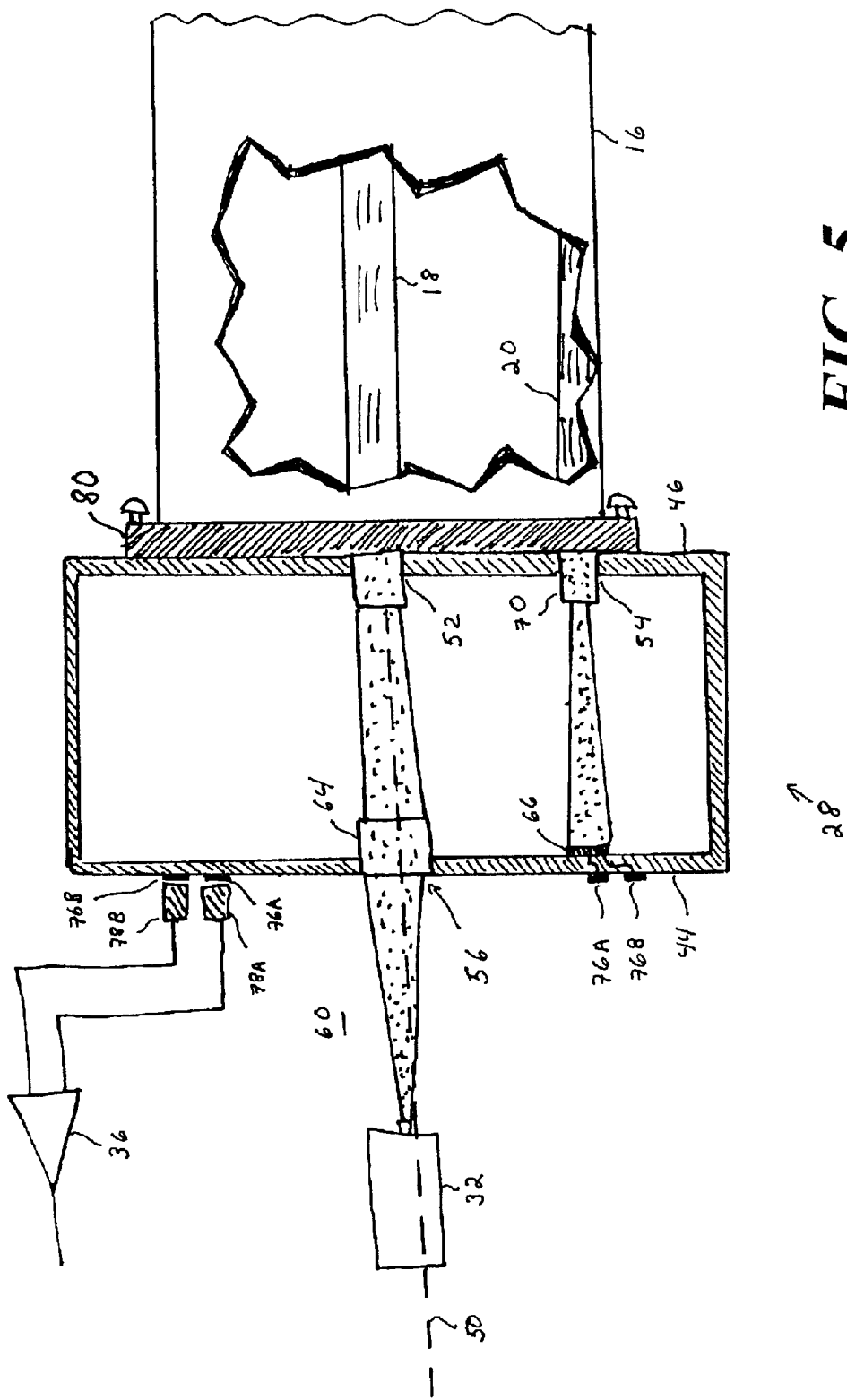

In another embodiment, shown in FIG. 5, the first optical relay 64 includes a first GRIN ("graduated index of refraction") lens seated in the central aperture 56. The second optical relay 70 includes a second GRIN lens seated in the eccentric port 54 for directing the collection beam 68 to a detector 66, now mounted on the inner wall of the proximal face 44. The slip rings 76A–B in this embodiment are mounted on the outer surface of the proximal face 44, where they make sliding contact with the brushes 78A–B as discussed in connection with FIG. 3.

In this second embodiment, the delivery and collection fibers 18, 20 do not actually penetrate the central and eccentric ports 52, 54. They are instead held against those ports by a mechanical fitting 80 on the distal face 46 of the housing 42. This enables the catheter 16 to be easily detached from the multi-channel coupler 28. Various fittings 80 are available for mechanically coupling to a fiber. Examples include sub-miniature type A connectors ("SMA"), face contact ("FC") connectors, and square connectors ("SC").

Coupler with External Detector

Figure 6:
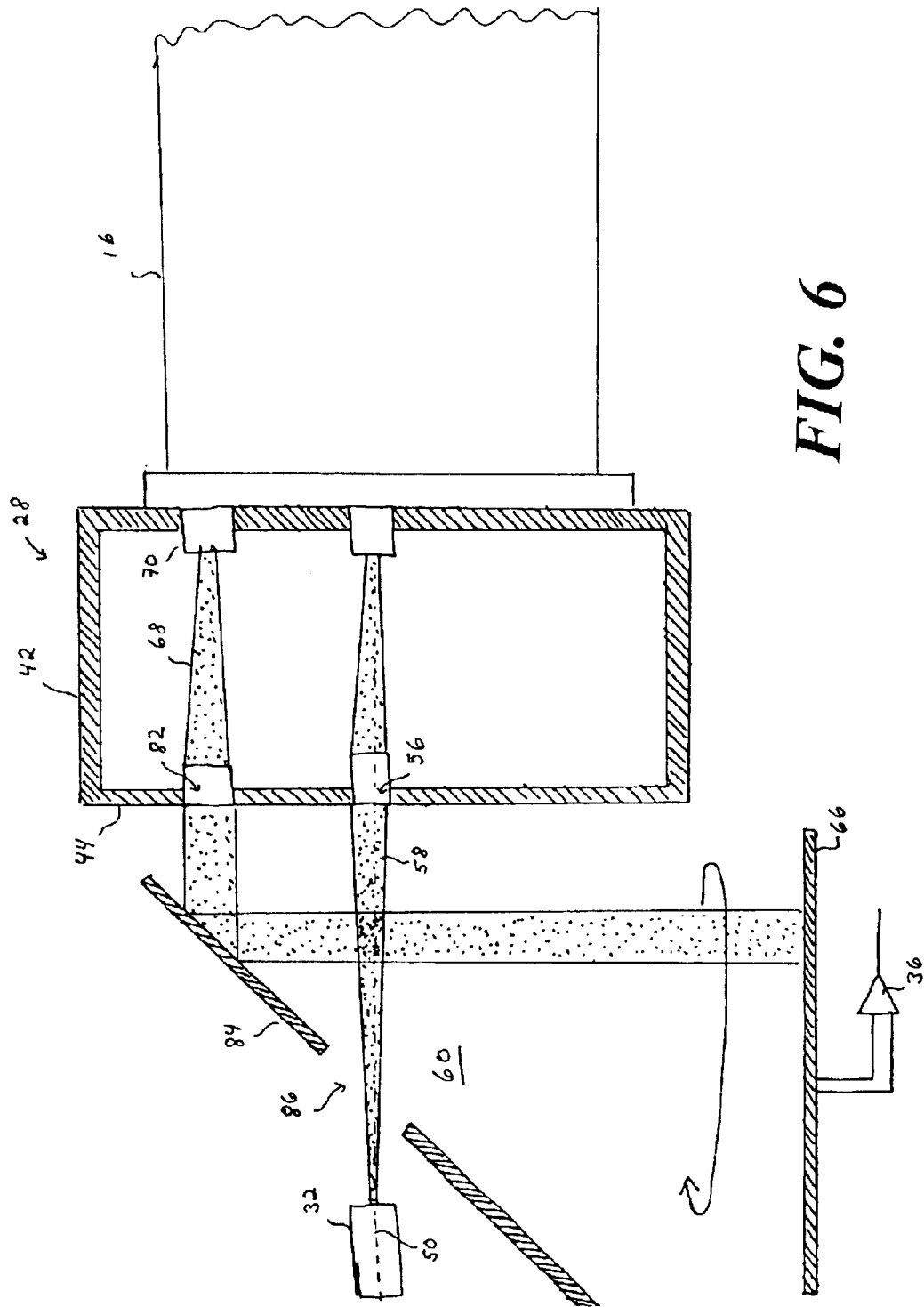

A third embodiment, shown in FIG. 6, dispenses with slip rings 76A–B and brushes 78A–B altogether by placing a detector 66 outside the housing 42. In this embodiment, the second optical relay 70 directs the collection beam 68 to an eccentric aperture 82 on the proximal face 44 of, and radially displaced from, the central aperture 56. As the housing 42 spins, the collection beam 68, which emerges from the eccentric aperture 82, traces a circular path similar to that shown in FIG. 4.

An annular mirror 84 in the gap 60 between the laser 32 and the housing 42 intercepts the circular path traced by the collection beam 68 and reflects it toward a detector 66. To permit the delivery beam 58 to proceed unimpeded into the central aperture 56 of the housing 42, the annular mirror 84 features a central hole 86 aligned with the axis 50.

The geometry of the annular mirror 84 is selected to encompass the path traced out by the collection beam 68 as the housing 42 spins about the axis 50. The detector 66 must likewise have a shape and extent to encompass the path traced out by the collection beam 68 as reflected by the annular mirror 84. Alternatively, the annular mirror 84 can be shaped to focus the path traced out on the mirror 84 onto a smaller path on the detector 66. Or, additional optical elements can be placed in the path followed by the collection beam 68 outside the housing 42 to cause the path traced out by the collection beam 68 to be mapped into another curve.

OTHER EMBODIMENTS

The optical couplers shown in FIGS. 1–6 are two-channel couplers. Each has a delivery channel that carries the delivery beam 58 and a collection channel for carrying a collection beam 68. However, additional collection channels can be added by providing additional collection ports, each of which is in communication with an additional collection fiber.

As described above, the second optical relay 64 relays scattered light brought to the eccentric port 54 by the collection fiber 20 while the first optical relay 64 delivers light out the central port 52 and into the delivery fiber 18. However, the collection fiber 20, the delivery fiber 18, and the first and second optical relays 64, 70 are all inherently bi-directional. Hence, the delivery fiber 18 and the first optical relay 64 can be used to both deliver light and collect light simultaneously. Similarly, the collection fiber 20 and the second optical relay 64 can be used to both deliver and collect light simultaneously. In addition, the collection fiber 20 and the second optical relay 64 can be used to deliver light while the delivery fiber 18 and the first optical relay 64 can be used to collect light. The ability of the delivery Fiber 18 and the first optical relay 64 to simultaneously deliver and collect light permits the concurrent performance of two or more procedures.

In the embodiments of FIGS. 3 and 5, additional optical relays can be provided to guide the additional collection beams to corresponding detectors. The detectors are them connected to additional slip rings, which relay a signal to the amplifier by way of additional brushes.

In the embodiment of FIG. 6, additional eccentric apertures can be provided in the proximal face. The collection beams emerging from these apertures form concentric nested traces on the annular mirror. The annular mirror then reflects these traces to form concentric traces on the detector. These traces can then be separated from each other by designating signals received from selected pixels of the detector to correspond only to particular collection beams. In particular, the selected pixels on the detector correspond to the loci of the various traces on the detector.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A multi-channel optical coupler comprising:
   a housing configured to spin about an axis, the housing having a proximal face and a distal face;
   walls forming a central aperture on the proximal face, the central aperture intersecting the axis;
   a first optical relay for guiding a first beam from the central aperture to a central port on the distal face; and
   a second optical relay for guiding a second beam to a detector from an eccentric port on the distal face
   wherein the first optical relay includes a stationary lens disposed to direct the first beam onto the central aperture.

2. The optical coupler of claim 1, wherein the first optical relay further comprises a focusing lens disposed between the stationary lens and the central port.

3. The optical coupler of claim 1, wherein the first optical relay comprises a graduated index of refraction lens seated in the central aperture, the graduated index of refraction lens being configured to direct the first beam to the central port.

4. A multi-channel optical coupler comprising:
   a housing configured to spin about an axis, the housing having a proximal face and a distal face;
   walls forming a central aperture on the proximal face, the central aperture intersecting the axis;
   a first optical relay for guiding a first beam from the central aperture to a central port on the distal face; and
   a second optical relay for guiding a second beam to a detector from an eccentric port on the distal face
   wherein the second optical relay includes a collimating lens within the housing, the collimating lens being disposed to guide the second beam entering the housing at the eccentric port toward a detector mounted on an inner wall of the housing.

5. The optical coupler of claim 4, wherein the second optical relay further comprises a light-directing element disposed to direct the second beam toward a peripheral wall of the housing.

6. A multi-channel optical coupler comprising:
   a housing configured to spin about an axis, the housing having a proximal face and a distal face;
   walls forming a central aperture on the proximal face, the central aperture intersecting the axis;
   a first optical relay for guiding a first beam from the central aperture to a central port on the distal face; and
   a second optical relay for guiding a second beam to a detector from an eccentric port on the distal face
   wherein the second optical relay includes:
   walls forming an eccentric aperture in the proximal face of the housing, the eccentric aperture being disposed to permit the second beam to pass therethrough; and an annular mirror outside the housing, the annular mirror being disposed to intercept a path traced by the second beam emerging from the eccentric aperture as the housing spins.

7. The optical coupler of claim 6, wherein the annular mirror comprises walls forming a mirror aperture disposed to permit the first beam to pass therethrough.

8. The optical coupler of claim 6, wherein the annular mirror is disposed to direct a path traced by the second beam onto a stationary detector.

9. A multi-channel optical coupler comprising:
a housing configured to spin about an axis, the housing having a proximal face and a distal face;
walls forming a central aperture on the proximal face, the central aperture intersecting the axis;
a first optical relay for guiding a first beam from the central aperture to a central port on the distal face;
a second optical relay for guiding a second beam to a detector from an eccentric port on the distal face; and
a slip ring disposed on an outer surface of the housing, the slip ring being in electrical communication with a detector within the housing.

10. A system for identifying vulnerable plaque, the system comprising:
a catheter having a collection fiber and a delivery fiber extending therethrough; a housing configured to spin about an axis, the housing having a proximal face and a distal face, the proximal face having walls forming a central aperture and the distal face being engaged with the catheter;
a first optical relay extending between the central aperture and a central port on the distal face, the central port being in optical communication with the delivery fiber; and
a second optical relay extending between a detector and an eccentric port on the distal face, the eccentric port being in optical communication with the collection fiber.

11. The system of claim 10, wherein the first optical relay comprises a lens disposed to receive a delivery beam passing through the central aperture and to direct the delivery beam into the central port.

12. The system of claim 10, wherein the lens comprises a graduated index of refraction lens seated in the central aperture.

13. The system of claim 10, wherein the second optical relay comprises a lens disposed in the housing to guide a collection beam from the eccentric port to the detector.

14. The system of claim 10, wherein the second optical relay comprises:
walls forming an eccentric aperture in the proximal face of the housing, the eccentric aperture being disposed to permit the second beam to pass therethrough; and
an annular mirror disposed outside the housing disposed to intercept a path traced by the collection beam emerging from the eccentric aperture as the housing spins.

15. The system of claim 14, wherein the annular mirror comprises walls forming a central aperture disposed to allow the collection beam to pass therethrough.

16. The system of claim 14, wherein the annular mirror is disposed to direct a path traced by the collection beam onto a stationary detector.

17. The system of claim 10, further comprising a slip ring disposed on an outer surface of the housing, the slip ring being in electrical communication with a detector within the housing.

18. A method for providing optical coupling to a collection fiber and a delivery fiber, the method comprising:
transmitting a delivery beam into a central aperture of a housing;
guiding the delivery beam from the central aperture to a central port in the housing, the central port being in optical communication with the delivery fiber;
receiving a collection beam from an eccentric port in the housing, the eccentric port being in optical communication with the collection fiber; and
guiding the collection beam to a detector by relaying the collection beam from the eccentric port to a detector within the housing.

19. The method of claim 18, wherein guiding the delivery beam comprises relaying the delivery beam from the central aperture to the central port.

20. A method for providing optical coupling to a collection fiber and a delivery fiber, the method comprising:
transmitting a delivery beam into a central aperture of a housing;
guiding the delivery beam from the central aperture to a central port in the housing, the central Port being in optical communication with the delivery fiber;
receiving a collection beam from an eccentric port in the housing, the eccentric port being in optical communication with the collection fiber; and
guiding the collection beam to a detector by
relaying the collection beam from the eccentric port to an eccentric aperture in the housing; and
relaying the collection beam from the eccentric aperture to a detector outside the housing.

21. The method of claim 20, wherein relaying the collection beam from the eccentric aperture to the detector comprises reflecting the collection beam off an annular mirror toward the detector.

22. The method of claim 21, wherein guiding the delivery beam comprises passing the delivery beam through a hole in the annular mirror.

* * * * *